United States Patent
Bossoutrot et al.

(10) Patent No.: US 8,409,504 B2
(45) Date of Patent: *Apr. 2, 2013

(54) METHOD FOR SUPPLYING GAS MIXTURES FOR AN ANALYZER

(75) Inventors: Valerie Bossoutrot, Guyancourt (FR); Joerg Koppel, Ludwigsburg (DE); Severine Lepic, Paris (FR); Herve Paoli, Rueil-Malmaison (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 293 days.

This patent is subject to a terminal disclaimer.

(21) Appl. No.: 12/745,026

(22) PCT Filed: Nov. 3, 2008

(86) PCT No.: PCT/FR2008/051977
§ 371 (c)(1),
(2), (4) Date: May 27, 2010

(87) PCT Pub. No.: WO2009/068767
PCT Pub. Date: Jun. 4, 2009

(65) Prior Publication Data
US 2010/0310419 A1    Dec. 9, 2010

(30) Foreign Application Priority Data
Nov. 27, 2007   (FR) ...................................... 07 59342

(51) Int. Cl.
*G01N 33/00*       (2006.01)

(52) U.S. Cl. ................................ 422/54; 422/88; 422/94
(58) Field of Classification Search .................... 422/54, 422/88, 94
See application file for complete search history.

(56) References Cited

U.S. PATENT DOCUMENTS

| | | | |
|---|---|---|---|
| 5,214,952 A | 6/1993 | Leggett et al. | |
| 5,524,473 A * | 6/1996 | Haskell | 73/1.03 |
| 6,562,088 B2 * | 5/2003 | Ukai et al. | 48/197 R |
| 2001/0032668 A1 | 10/2001 | Doty et al. | |

FOREIGN PATENT DOCUMENTS

| | | |
|---|---|---|
| CN | 1883783 | 12/2006 |
| DE | 19 842 413 | 10/1999 |
| JP | 6 194353 | 7/1994 |
| JP | 8 262000 | 10/1996 |
| JP | 2000 516713 | 12/2000 |

OTHER PUBLICATIONS

PCT/FR2008/051977 Written Opinion dated May 12, 2009.
PCT International Search Report for PCT/FR2008/051977.

* cited by examiner

*Primary Examiner* — Sam P Siefke
(74) *Attorney, Agent, or Firm* — Allen E. White

(57) ABSTRACT

The invention relates to a fluid analysis device that comprises an analyzer and a system for supplying an instrumentation gas to said analyzer, characterized in that the supply system includes at least one mixer generating said instrumentation gas, and at least one purifier located downstream from said at least one mixer and upstream from said analyzer.

9 Claims, 2 Drawing Sheets

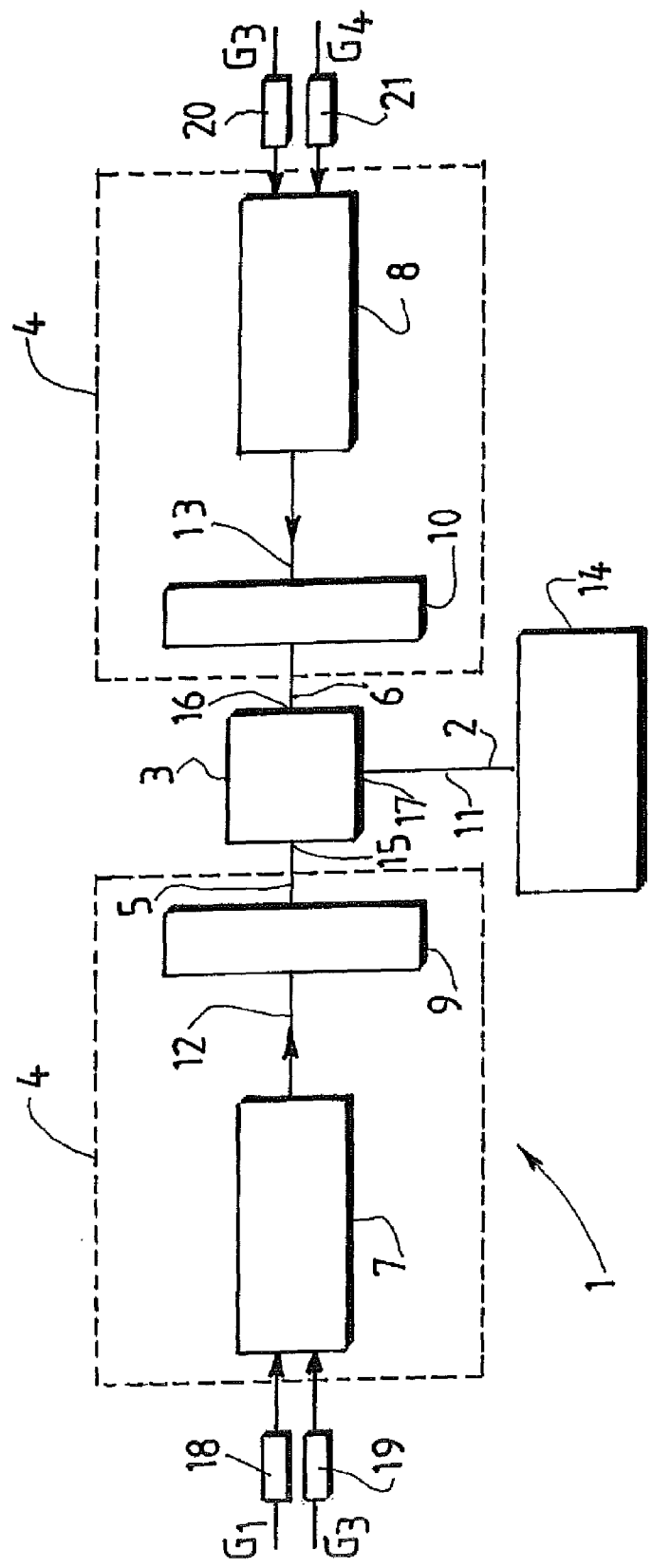

METHOD FOR SUPPLYING GAS MIXTURES FOR AN ANALYZER

CROSS-REFERENCE TO RELATED APPLICATIONS

This application is a §371 of International PCT Application PCT/FR2008/051977, filed Nov. 3, 2008.

BACKGROUND

1. Field of the Invention

The present invention relates to a device for analyzing a fluid and to a method of delivering at least one gas mixture especially to a fluid analyzer.

The analyzable fluids may be either gases or liquids. They may be obtained by direct sampling on an industrial process for the purpose of quality control or by sampling a given atmosphere, for example the ambient air, for monitoring or control purposes.

2. Related Art

The analyzers used for measuring small concentrations of chemical species in a fluid sample are sensitive to the characteristics of the pure gases and gas mixtures with which they are supplied. Pure gases or gas mixtures are used to convey the specimen right to the detector and to set a "zero" point during calibration, this being essential in the fluid analysis field. They may also serve to operate the device itself. These pure gases or gas mixtures are called instrumentation gases. For example, these instrumentation gases are helium, nitrogen, air or mixtures such as $H_2/He$, $H_2/Ar$, $CH_4/Ar$, $CO_2/Ar$ and $H_2/N_2$.

The content of impurities present in these instrumentation gases and the specifications for producing them are parameters that have an influence on the sensitivity of the analyzers and the reproducibility of the analyses.

The levels and nature of the impurities contained in the instrumentation gases enable a quality equivalent to a purity of 99.999% to be achieved. The most frequently guaranteed impurities are moisture and hydrocarbons. Carbon oxides (CO and $CO_2$) and oxygen may also form the subject of guarantees.

Because of ever more stringent regulations, analytical laboratories have to measure ever lower concentrations. The improvement in the performance of analyzers is consequently focused on their detection limit and their precision. The guarantees offered today in the case of instrumentation gases are no longer sufficient to meet these requirements, both in terms of purity and production precision. This is because the impurities present with too high a concentration disturb the background noise of analyzers, thus downgrading their sensitivity. The range of guaranteed impurities may be insufficient and become a source of interference in the measurements. For example, guaranteed impurities are moisture and oxygen, whereas those that are critical for analysis are hydrocarbons, an additional specification enabling interference on the analyses to be limited. Finally, the difference between the deviations in composition from one mixture to another, which is too high compared with the theoretically intended production of the proportions of the various components of the instrumentation gases, is a source of imprecision in the analytical results.

The particular example of a flame ionization detector (FID) as analyzer consists of a flame supplied with a hydrogen/helium mixture and with air, and a collecting plate. The specimen to be analyzed passes through a flame which decomposes the organic molecules and produces ions. These are recovered on a biased electrode and thus produce an electrical signal. An FID is extremely sensitive and provides a wide dynamic range. FIDs are used for detecting hydrocarbons, such as for example methane, ethane or even acetylene. The specimen to be analyzed is mixed beforehand with the combustible instrumentation mixture in a preheated zone. The ions and the electrons formed in the flame are collected and thus enable a current to flow in an external circuit. The current is proportional to the amount of ions, which depends on the concentration of hydrocarbons in the fluids to be analyzed. The current is detected by a suitable electrometer and is displayed on an analog output. Thus, an FID provides a rapid, precise (down to ppb) and continuous reading of the hydrocarbon concentration.

The FID is supplied with two gas mixtures, namely hydrogen/helium ($H_2/He$) in well-defined respective proportions, for example 40% and 60%, and oxygen/nitrogen ($O_2/N_2$) in well-defined respective proportions, for example 20% and 80%. The variation in deviations relative to the theoretically intended production of the proportions of the various components from one mixture to another constitutes a source of uncertainty about the results of the analyses carried out using an FID. To improve the reliability of analyses carried out by FID, the $H_2/He$ and $O_2/N_2$ mixtures, called flame gases, must therefore have steady production precision levels from one mixture to another, thus enabling the influence of this parameter on the measurements to be limited. Furthermore, the content of impurities present in the instrumentation gases is also a factor to be taken into consideration, the more so when small amounts (less than or equal to one part per million) have to be analyzed by FID.

These specifications must therefore be improved in order to ensure reliability of the analyses.

For example in the case of FIDs, the flame gases today are delivered in bottle form with production precision levels between 1 and 2% absolute for the hydrogen content in the case of an $H_2/He$ mixture and between 0.5 and 1% absolute for the oxygen content in the case of an $O_2/N_2$ mixture. The variation in composition of these mixtures from one bottle to another is a source of error for the end customer. This is because a variation of 2% absolute in the $H_2$ concentration in the $H_2/He$ mixture may generate up to a 30% variation in the FID signal obtained for analyzing hydrocarbons. Likewise, a 2% variation in the oxygen content in the $O_2/N_2$ mixture supplying the FID generates a 10% variation in the FID signal.

Furthermore, the impurity content is a critical parameter as regards analysis reliability. An impurity concentration of 40 ppb generates a 23% increment in the signal when a zero air sample is analyzed by total FID. However, at the present time the usually guaranteed level of impurities in a bottled mixture is between 50 and 100 ppbv. For example in the case of FIDs, the delivery of bottles of $H_2/He$ and $O_2/N_2$ mixtures for supplying FIDs therefore has the drawback of generating large uncertainties in the analytical results, which will be all the more critical the lower the contents to be analyzed. The delivery of such bottled mixtures therefore does not guarantee reproducibility over time, either in their composition or in their purity.

This guarantee corresponds to a method of preparing the containers and filling them with mixtures that enables a large number of products to be produced at economically viable costs. The change in requirements in terms of precision and guaranteed levels of impurity means that the production of these bottled mixtures would necessitate modifying the existing processes and plants, something which would incur a significant increase in production costs. Thus, it seems that, for these types of mixtures, the limits in production precision levels achieved by filling centers have today been reached, at the very least for manufacturing a large number of these mixtures. As regards impurities, the guaranteed levels fluctuate depending on the sources used, the process for producing the gas bottles and the method of filling these bottles.

SUMMARY OF THE INVENTION

One object of the present invention is to alleviate some or all of the abovementioned drawbacks.

For this purpose, the invention consists of a device for analyzing a fluid, comprising:
an analyzer; and
a feed system for supplying said analyzer with instrumentation gases,
characterized in that the feed system comprises at least one mixer that generates said instrumentation gas and at least one purifier located downstream of said at least one mixer and upstream of the analyzer.

According to one embodiment of the invention, the system for supplying said analyzer with instrumentation gases further includes at least one purifier located upstream of at least one mixer.

The advantage of having a single purifier downstream of the mixer is that it simplifies the entire delivery process. However, the addition of a purifier upstream of the mixer makes it possible to remove specific impurities from at least one of the pure gases upon entry that it would not be possible to remove from the final mixture because of technical and/or safety constraints.

Moreover, embodiments of the invention may include one or more of the following features:
the analyzer is a flame ionization detector.
The analyzer may also be chosen from the following list: katharometer (or TCD), electron capture detector (ECD), photoionization detector, chemiluminescence detector, electrochemical detector, helium ionization detector, glow discharge detector, plasma emission detector, atomic emission detector, reducing gas analyzer;
for example, a flame ionization detector is supplied with two instrumentation gas mixtures, one being a hydrogen/helium mixture and the other an oxygen/nitrogen mixture, the feed system being formed by a first purifier located downstream of a first mixer that generates the hydrogen/helium mixture and upstream of the analyzer and by a second purifier located downstream of a second mixer that generates the oxygen/nitrogen mixture and upstream of the analyzer;
in particular when the analyzer to be supplied is a flame ionization detector, the hydrogen/helium mixture has respective proportions of 35% to 45%, preferably 40%, hydrogen and 55% to 65%, preferably 60%, helium and the oxygen/nitrogen mixture has respective proportions of 15% to 25%, preferably 20%, oxygen and 75% to 85%, preferably 80%, nitrogen;
said at least one mixer comprises a component chosen from a mass flow rate regulator, sonic orifices, sets of calibrated orifices of different diameters, or regulating valves. The parameterization of predefined thresholds for mass flow rate regulators or the use of sets of calibrated orifices of different diameters makes it possible to generate mixtures of different concentrations and/or to vary the total flow rate. Components such as regulators or pressure sensors and pneumatic valves may be integrated into said at least one mixer in order to ensure optimum operation of the flow rate regulating members; and
said at least one purifier may, depending on the entry gas and the type of impurity to be eliminated, be composed of one or more elements chosen from the following elements: a particulate filter, a catalyst comprising noble metals and/or metal oxides, a cryogenic trap, one or more adsorbents possibly distributed as several successive beds, such as for example active carbon, activated alumina, or various types of zeolite.

In one embodiment of the invention, said at least one purifier may also include an alarm or warning, such as an audible or visual signal, or another message indicating that the purifier has reached the end of its guaranteed lifetime. Such a device enables the user to be informed so that he can either change the purifier or switch to an emergency supply offering him the same specifications. As a variant, this alarm may be coupled to an automatic mixer shutoff in order to prevent erroneous analyses because of the deterioration in the performance of the purifier.

The emergency supply may either consist of a bottled gas of known composition or a switch to another purifier.

As an additional variant, the purification is provided by a self-regenerated purification means. Such a purification means is for example a PSA (pressure swing adsorption) or TSA (temperature swing adsorption) unit. In the latter two examples, two tanks are placed in parallel with the flow of the gas and are filled with an adsorbent (such as active carbon, activated alumina or a zeolite). When the first tank is enabling the gas to flow to the mixer, the second is in regeneration mode. This regeneration may take place by means of a change in pressure (PSA unit) or an increase in temperature under a stream of gas (TSA unit).

According to one embodiment of the invention, a pressure regulator is located downstream of said at least one purifier.

Another subject of the invention is a feed system for supplying a fluid analyzer with instrumentation gases, consisting of at least one mixer which generates said instrumentation gas combined with at least one purifier located downstream of said at least one mixer, said feed system being integrated into one and the same fluid analysis device.

Another subject of the invention is a feed system for supplying a flame ionization detector with instrumentation gases, formed by two mixers each generating an instrumentation gas mixture, each mixer being located upstream of a purifier.

Another subject of the invention is the use of a feed system as described above, for delivering at least one instrumentation gas mixture to a fluid analyzer.

Yet another subject of the invention is a method of delivering at least one gas mixture to a fluid analyzer, comprising the following steps:
a) a mixture of at least two pure gases is formed using a mixer; and
b) the mixture obtained in step a) is purified by means of a purifier that generates an instrumentation gas mixture for said analyzer,
characterized in that these steps are carried out on one and the same site by means of a single piece of equipment.

Such a method may further include, prior to step a), a step of purifying at least one gas to be mixed.

Yet another subject of the invention is a method of delivering two gas mixtures to a flame ionization detector, comprising the following steps:
a) formation of a first mixture consisting of 40% hydrogen and 60% helium, employing a first mixer, and formation of a second mixture consisting of 20% oxygen and 80% nitrogen, employing a second mixer; and b) purification of the first mixture obtained in step a) by means of a first purifier that generates a first instrumentation gas mixture for the flame ionization detector and purification of the second mixture obtained in step a) by means of a second purifier that generates a second instrumentation gas mixture for said flame ionization detector, characterized in that these steps are carried out on one and the same site by means of a single piece of equipment.

BRIEF DESCRIPTION OF THE FIGURES

Other features and advantages will become apparent on reading the description below, given with reference to FIGS. 1 and 2:

FIG. 2 shows a diagram of a variant of a device according to the invention for analyzing a fluid.

DETAILED DESCRIPTION OF THE INVENTION

Figure 1:
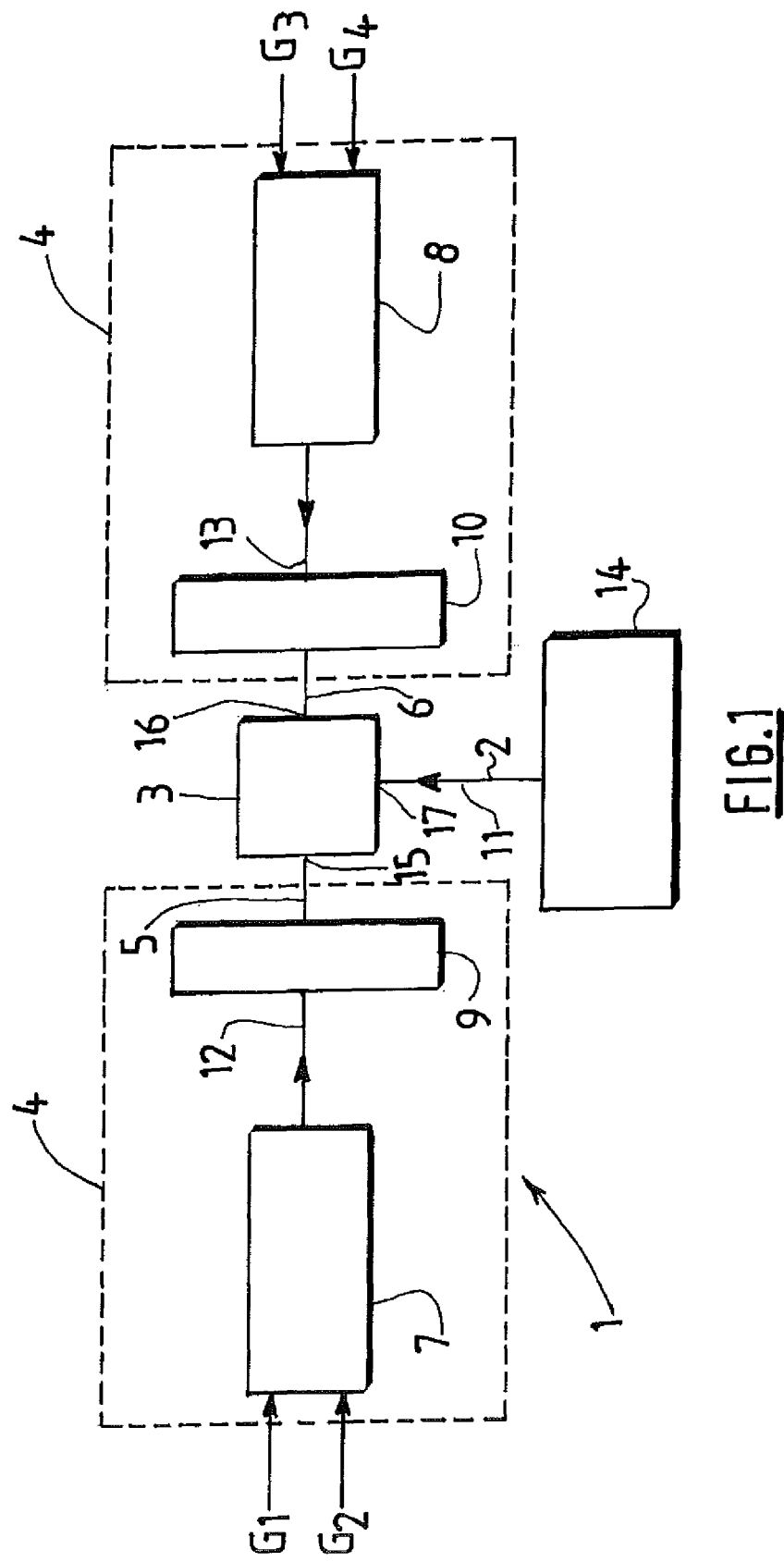
FIG. 1 shows a diagram of a device according to the invention for analyzing a fluid.

FIG. 1 shows a device 1 for analyzing a fluid 2 contained in a reservoir 14. The fluid 2 is for example a sample of the ambient air or a sample of an exhaust gas. The device 1 consists of equipment 4 or a system for supplying an analyzer 3 with instrumentation gases. The equipment 4 here consists of two identical parts, each formed from a purifier 9 or 10 located downstream of a mixer 7 or 8. The entry gases G1 to G4 are pure gases such as, for example, helium, nitrogen, hydrogen, argon, methane or carbon dioxide. These pure gases are in particular delivered in bottle form or from generators. Their specifications in terms of impurities are compatible with the purification capabilities of the purifier 9 or 10 placed upstream of the analyzer 7 or 8.

The existing technologies for the mixer 7 or 8 allow mixtures 5 or 6 to be generated with an uncertainty not exceeding 0.5% absolute in the concentration of the minor component. It may involve mass flow rate regulators or sonic orifices or regulating valves.

The purifier 9 or 10 is used to reduce the content of impurities that are critical for the analysis. For example, the purifier may be a catalyst composed of metal oxides in order to convert hydrocarbons to $CO_2$ and $H_2O$. It may be combined with adsorbents for trapping these impurities in order to limit their impact on the measurement.

All this gas mixture delivery equipment enables precise mixtures having low impurity contents to be generated. The subject of the present invention, which constitutes an alternative to bottled mixtures, is a means for reducing the contribution played by analyzer supply mixtures to analytical uncertainty.

Pure gases, such as G1 and G2 (or G3 and G4), enter the mixer 7 (or alternatively 8), said mixer delivering a mixture G1/G2 flowing in a line 12 (or alternatively G3/G4 flowing in a line 13). The purifier 9 (or alternatively 10) serves to reduce the content of critical impurities of the mixture G1/G2 (or alternatively G3/G4) and thus deliver a mixture 5 (or alternatively 6). The mixtures 5 and 6 each represent an instrumentation gas for analyzing the fluid 2 coming from the reservoir 14. Said fluid 2 flows in a line 11 into the analyzer 3, into which the instrumentation gases also flow. According to one particular embodiment of the invention, the equipment 4 is made up of a single section. A section consists of a mixer 7, a purifier 9 and a line 12 in which the instrumentation gas 5 flows. A device according to the invention may also comprise equipment 4 consisting of more than two sections.

If the analyzer 3 is a flame ionization detector, the instrumentation gas supply system or equipment 4 comprises a first purifier 9 located downstream of a first mixer 7, which generates a hydrogen (G1)/helium (G2) mixture 5 flowing in the line 12. A second purifier 10 is located downstream of a second mixer 8, which generates an oxygen (G3)/nitrogen (G4) mixture 6 flowing in the line 13. This purifier 10 is located upstream of the analyzer 3 intended to analyze the fluid 2 coming from the specimen 14, said fluid flowing in the line 11 into the analyzer 3 via the inlet 17.

The mixtures 5 and 6 supply the analyzer 3 via the inlets 15 and 16 and conduct the fluid 2 of the specimen 14 into that part of the analyzer 3 in which the measurements will be carried out. These flame gases 5 and 6 also serve to set a "zero" point when calibrating the analyzer 3.

FIG. 2 shows a device 1 for analyzing a fluid 2 contained in a reservoir 14. Unlike the device shown in FIG. 1, the device shown schematically here further includes at least one purifier 18, 19, 20, 21 placed upstream of at least one mixer 7 or 8. As a consequence, at least one of the pure gases to be mixed may be purified before entering the mixer. The addition of a purifier upstream of the mixer enables specific impurities to be removed from at least one of the incoming pure gases G1 to G4 that could not be removed from the final mixture because of technical and/or safety constraints. According to the objectives to be achieved, just one entry gas will be purified upstream of at least one mixer 7 and 8, or else several entry gases will be purified before being mixed. Finally, according to one embodiment of the invention, all the gases to be mixed will firstly be purified.

In general, the solution proposed by the present invention therefore consists, on the one hand, of a mixer allowing on-site generation of the instrumentation gases and, on the other hand, of a purifier placed downstream of the mixer and upstream of the analyzer. These two components are combined and constitute a single piece of equipment.

The mixer makes it possible to ensure that the composition of the mixture is stable over time. It may be made up either of mass flow rate regulators or sonic orifices, depending on the flow dynamics desired by the customer. The purifier serves to remove the critical impurities, for example hydrocarbons, by converting them to $CO_2$ and $H_2O$, for example using a catalytic process. This purifier may also comprise an adsorbent in successive beds for trapping these impurities, for example a sieve first bed for trapping $H_2O$ and a zeolite second bed for trapping $CO_2$.

The components of the mixer make it possible to achieve a mixture production precision in the concentration of the minor component of 0.5% absolute or better. Production on the customer's site obviates potential fluctuations in the concentrations of the mixtures forming the instrumentation gases. For example in the case of an FID, production on the customer's site obviates potential fluctuations of the hydrogen concentration in the $H_2$/He mixture or the oxygen concentration in the $O_2/N_2$ mixture. By guaranteeing this precision, reproducibility of the customer's analyses is improved.

The purifier enables a level of hydrocarbon impurities to be achieved upstream of the analyzer that is below that disturbing its analysis. Its continuous operation enables the "background noise" of the analyzer to be maintained at satisfactory levels for analyzing low hydrocarbon contents. In the case of FIDs, the critical impurities are hydrocarbons—for analysis of 100 ppbv of hydrocarbons, the purifier must achieve hydrocarbon contents below 10 ppbv.

The complete equipment provides the customer with a guarantee that the composition of the mixture is stable over time, thanks to the precision of the mixer, and that the purity delivered at the point of use is constant, thanks to the performance of the purifier. This solution therefore has the advantage of providing the customer with a mixture having essential characteristics that are stable over the course of time. Thus the proposed solution helps to reduce the contribution played by the analyzer feed gases to the uncertainty of the analyses. Furthermore, combining mixer and purifier offers the customer greater ease of use and faster operation compared with bottled delivery.

It should be obvious that the present invention allows for embodiments in many other specific forms without it departing from the field of application of the invention as claimed. Consequently, the present embodiments must be considered as illustrations, but they may be modified within the field defined by the scope of the appended claims, and the invention should not be limited to the details given above.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A device for analyzing a fluid, comprising:
   an analyzer; and
   a feed system for supplying said analyzer with instrumentation gases, characterized in that the feed system comprises at least one mixer that generates said instrumentation gas and at least one purifier located downstream of said at least one mixer and upstream of the analyzer, the feed system further defined as comprising:
      four instrument calibration sources containing hydrogen, helium, oxygen and nitrogen (G1-G4) in fluid communication with the feed system and wherein the feed system is configured to form two instrumentation gas mixtures (G1-2, G3-4), one being a hydrogen/helium mixture and the other an oxygen/nitrogen mixture;
      the at least one mixer comprises first and second mixers, the first mixer configured to mix the hydrogen and helium and the second mixer generates the configured to mix the oxygen and the nitrogen;
      the at least one purifier comprises first and second purifiers;
      the first purifier being located downstream of the first mixer and upstream of the analyzer; and
      the second purifier being located downstream of the second mixer and upstream of the analyzer.

2. The device of claim 1, wherein the system for supplying said analyzer with instrumentation gases further includes at least one purifier located upstream of at least one mixer.

3. The device of claim 1, wherein the analyzer is a flame ionization detector.

4. The device of claim 1, wherein:
   the hydrogen/helium mixture includes 40% hydrogen and 60% helium; and
   the oxygen/nitrogen mixture includes 20% oxygen and 80% nitrogen.

5. The device of claim 1, wherein said at least one mixer comprises at least one component chosen from a mass flow rate regulator, sonic orifices, sets of calibrated orifices of different diameters, and regulating valves.

6. The device of claim 1, wherein said at least one purifier comprises one or more elements chosen from a particulate filter, a catalyst comprising noble metals and/or metal oxides, and a cryogenic trap.

7. The device of claim 1, wherein said at least one purifier also includes at least one adsorbent.

8. The device of claim 1, wherein at least one purifier also includes a warning system adapted to warn that the purifier is coming to the end of its guaranteed lifetime.

9. The device of claim 1, wherein a pressure regulator is located downstream of said at least one purifier.

* * * * *